United States Patent [19]

Oppici et al.

[11] Patent Number: 4,568,740

[45] Date of Patent: Feb. 4, 1986

[54] PROCESS FOR PURIFYING TYLOSIN

[75] Inventors: Ernesto Oppici, Milan; Onorino G. Rosa, San Raffaela Cimema; Carlo Varesio, Turin; Giovanni Lazzari; Danillo Fabris, both of Settimo Torinese, all of Italy

[73] Assignee: Farmitalia Carlo Erba S.p.A., Milano, Italy

[21] Appl. No.: 594,318

[22] Filed: Mar. 28, 1984

[30] Foreign Application Priority Data

Mar. 30, 1983 [IT] Italy .............................. 20359 A/83

[51] Int. Cl.$^4$ ............................................. C07H 17/08
[52] U.S. Cl. ...................................... 536/7.5; 536/7.1; 536/16.9
[58] Field of Search ....................... 536/7.1, 16.9, 7.5

[56] References Cited

U.S. PATENT DOCUMENTS 2,827,417 3/1958 Friedman et al. ................. 536/16.9
3,629,233 12/1971 Fujita et al. ........................... 536/7.5

FOREIGN PATENT DOCUMENTS 901273 7/1962 United Kingdom .

Primary Examiner—Johnnie R. Brown
Assistant Examiner—Elli Peselev
Attorney, Agent, or Firm—Oblon, Fisher, Spivak, McClelland & Maier

[57] ABSTRACT

Disclosed is a process for purifying Tylosin by selective adsorption of the fermentation broth previously brought to 7.5–10.0 pH on polymeric resins and by subsequent deadsorption of the purified product with a aqueous-alcoholic or aqueous-acetonic solution and further purification of the eluate by filtration through macroreticular weak anion resins.

3 Claims, No Drawings

PROCESS FOR PURIFYING TYLOSIN

BACKGROUND OF THE INVENTION

1. Field of the Invention

The present invention relates to a process for purifying Tylosin by selective adsorption on polymeric resins.

2. Description of the Background

As reported in both the scientific and patent literature, Tylosin base is usually extracted from the fermentation broth previously brought to a pH of 8.5 by chlorinated organic solvents, such as dichloromethane or chloroform or nonchlorinated solvents such as methylisobutylketone.

The combined organic extracts are then concentrated in vacuo and, after decoloration with activated carbon, Tylosin base precipitates by addition of n-hexane.

Alternatively, Tylosin base can be transferred from the organic extract into an aqueous phase in the form of a soluble salt by neutralization with a suitable organic or inorganic acid (tartaric or phosphoric acid). The aqueous solution containing the soluble salts of Tylosin is successively dried in vacuo (spray-drier) to obtain the antibiotic in the form of salt of the acid used.

According to the methods above described, it is not possible to reach a complete elimination of the impurities present, in same cases, in particularly high amounts in the fermentation broth, so that the quality of the final product depending on the type of these impurities (colors or fermentation by-products) is often unsatisfactory both in the titer and in the analytical and organoleptic properties.

The invention eliminates the above mentioned inconveniences and discloses a new method for purifying Tylosin which is very simple and allows one to obtain a product having the specifications in accordance with the requirements.

SUMMARY OF THE INVENTION

The purification process of the invention comprises a selective adsorption of Tylosin in the fermentation broth on an adsorbing resin ER-180 ® (Rohm and Haas) or on other types of polymeric resins such as Amberlite ® (XAD$_2$; XAD$_4$—Rohm and Haas); type Daion ® (HP 20; HP 21; HP 30; HP 40; HP 50—Mitsubishi); type Duolite ® (S 861; S 862; S 863; S 866—Diamond Shamrock); type Kastel ® (S 112—Montedison); Lewatite ® (OC 1031—Bayer A. G.).

It is evident, therefore, to any skilful in the art that the peculiar object of the purification process of the invention is primarily having found the adsorption conditions, the suitable solvents or mixtures of solvents to be used in the de-adsorption reaction, the right pH range, the subsequent operations all permit obtaining a final product in accordance with the required specifications.

DESCRIPTION OF THE PREFERRED EMBODIMENTS

The new purification process, briefly described herein below and described more in detail in the Examples comprises filtering the fermentation broth and bringing the filtrate containing Tylosin to pH 7.5–10 by addition of an aqueous solution of NaOH followed by adsorbing the tylosin on the polymeric resin.

In the cited pH values, the most amount of colored impurities present in the broth is eliminated with the effluent which Tylosin base is adsorbed on the resin. It is important to point out another advantage of this process which results from a very high adsorption capability of the resin towards the product (40–50 g/l) and the possibility for reusing the resin for a subsequent reaction after the de-adsorption step carried out with aqueous alcoholic or aqueous acetonic solution.

Only after 20–30 operating cycles, depending also on the type of the impurities contained in the fermentation broth, it is necessary to regenerate the same resin which is easily carried out with a mixture of water: isopropyl alcohol (70:30) and 4% NaOH. The de-adsorption of Tylosin base from the resin is carried out as above mentioned, by a mixture of water:isopropyl alcohol or water:acetone in the ratio 1:1 preferably.

The eluate thus obtained is adsorbed on a macroreticular weak anionic resin of the type IRA 35 ® (Rohm and Haas) to reach a complete decoloration.

Other resins of the type Lewatite ® (CA 9 222—Bayer) or Kastel[5] (A-105—Montedison) can be alternatively used. After concentration in vacuo and adjusting the pH, Tylosin base precipitates from the eluate by salting; yielding about 80%.

From Tylosin base thus purified it is possible to obtain its salts (tartrate, phosphate) by treatment with a stoichiometric amount of acid in an aqueous alcoholic environment and the solution obtained by filtration through decolorating carbon is concentrated to dryness. Alternatively, it is possible to obtain these salts directly by treating the purified eluate and subsequently by spray-drying the solution.

The following examples illustrate the process of the invention without limiting it.

EXAMPLES

EXAMPLE 1

Purification of Tylosin base 440 kg of fermentation broth were treated with Dicalite (3%) and then filtered on a rotating filter. The filtered broth so obtained (615 liters) containing 94% of the starting useful activity was brought to pH 7.5 by addition of 20% NaOH and adsorbed on a resin ER-180 ® (Rohm and Haas) in a column at a flow rate of 150 l/h (volume of the resin 100 l; diameter of the column 22.5 cm). The exhausted broth did not show any activity as checked by titration. The column was then washed with 200 l of water at a flow rate of 150 l/hr; the water of this washing did not contain any activity. Subsequently, the column was eluted with a mixture of water: isopropyl alcohol or water: acetone in the ratio of 1:1 and after elimination of 50 l of a lead fraction containing no activity, 100 l of the central eluate containing 90% of the starting activity was finally collected.

This eluate was concentrated and subsequently adsorbed on IRA 35 ® resin (Rohm and Haas) in a column, previously prepared at a flow rate of 20 l/hr.

The decolored eluate, thus obtained was brought to +10° C. and to a pH of about 8.5 by addition of an aqueous solution of NaOH and it was treated with 4.5 kg of sodium chloride.

After stirring for 2 hours at 35° C., the precipitated Tylosin base was filtered through a Buchner filter and washed with 8 l of water having pH 8.5 and a temperature of 45° C. The washed panel was dried in vacuo at 45° C. for 8 hours and subsequently in high vacuo for 6 hours.

The yield, calculated on the starting useful activity, is about 80% of Tylosin base corresponding to the normal specifications.

EXAMPLE 2

Preparation of Tylosin tartrate (neutral)

1 kg of purified Tylosin base, obtained according to Example 1, was suspended in 3,0 l of methyl alcohol and treated with 0.066 of tartaric acid and 0.05 kg of active carbon. After stirring for 30 minutes at room temperature, the mixture was filtered on Dicalite (0.10 kg), the panel was washed with 1.0 l of methanol and the filtrate was concentrated in vacuo (temperature of vapors 20°–25° C.) to dryness.

The dry, friable residue, thus obtained, was further dried in an oven in vacuo for 3 hours at 50° C. and then it was sieved. 911.5 g of Tylosin tartrate at 98.5% of useful activity were obtained.

EXAMPLE 3

520 kg of fermentation broth were treated, as described in the Example 1, to obtain the decolored and purified eluate. The eluate was added with 396 g of tartaric acid and the pH was brought to 6.0–6.4. Subsequently, 300 g of active carbon were added to the reaction mixture and maintained under stirring for 30 minutes at room temperature. After filtration on Dicalite, the solution was concentrated in vacuo to a volume, of about 25 l and then was spray dried. 4400 g of Tylosin tartrate at 98% of useful activity were obtained.

EXAMPLE 4

520 kg of fermentation broth were treated as described in Example 1 to obtain the central eluate. Subsequently, this eluate was concentrated in vacuo down to 70 l with simultaneous elimination of isopropanol. 35 l of methylene chloride were added and the pH was brought to 8.5 by addition of a 20% aqueous solution of NaOH.

After stirring for 15 minutes, the organic extract was separated, concentrated in vacuo down to 9.0 l and treated with 30.0 l of cyclohexane under stirring. The reaction mixture was maintained under stirring at a temperature of 10° C.–15° C. for about 3 hours and the precipitate separated by filtration was dried in vacuo at 40° C. for 4 hours.

4600 g of Tylosin base at 95% of useful activity were obtained.

EXAMPLE 5

490 kg of fermentation broth were treated as described in Example 1 while carrying out the adsorption on 100 l of Kastel ® S 112 resin.

After washing of the resin with deionized water, Tylosin base was eluted with 300 l of a mixture of acetone: water in the ratio of 2.3:1 at a flow rate of B/v/hr.

100 l of the central eluate was collected and treated with a 12% solution of $H_3PO_4$ up to pH 5.5 and was subsequently concentrated in vacuo up to 10 l to obtain a concentrated solution corresponding to 5000 g of Tylosin phosphate.

We claim:

1. A process for purifying tylosin by removing inorganic and organic impurities therefrom, which comprises:

filtering a fermentation broth which contains tylosin, thereby producing a solution containing said tylosin;

adjusting the pH of said solution to about 7.5–10.0 by the addition of an aqueous solution of NaOH, thereby producing a pH-adjusted solution;

adsorbing tylosin from said solution onto a polymeric resin;

eluting the adsorbed tylosin from the polymer resin with a mixture of water-isopropanol or water-acetone;

readsorbing the eluate on a macroreticular weak anionic resin;

concentrating the filtrate obtained from said readsorption step;

adjusting the pH of the filtrate to about 8.5;

precipitating tylosin from solution by the salting out effect; and isolating the purified tylosin.

2. The process of claim 1, wherein said tylosin is isolated by reacting purified tylosin with a stoichiometric amount of tartaric acid or phosphoric acid, thereby converting said tylosin to its tartaric acid salt or its phosphoric acid salt, and isolating the purified tylosin by spray-drying a solution containing one of said tylosin salts.

3. The process of claim 1, wherein said water-isopropanol and water-acetone mixtures are 1:1 mixtures.

* * * * *